United States Patent
Choi et al.

(10) Patent No.: US 6,227,052 B1
(45) Date of Patent: May 8, 2001

(54) METHOD FOR TESTING PHOTOINDUCED DOMAIN SWITCHING OF FERROELECTRIC CERAMICS USING ACOUSTIC EMISSION

(75) Inventors: Si Kyung Choi; Dong Gu Choi; Sung Ryul Kim, all of Taejeon (KR)

(73) Assignee: Korea Advanced Institute of Science and Technology, Taejeon (KR)

( * ) Notice: Subject to any disclaimer, the term of this patent is extended or adjusted under 35 U.S.C. 154(b) by 0 days.

(21) Appl. No.: 09/340,063

(22) Filed: Jun. 25, 1999

(30) Foreign Application Priority Data

Jun. 26, 1998 (KR) .................................................. 98-24379

(51) Int. Cl.[7] .................................................. G01N 29/04
(52) U.S. Cl. .............................................. 73/587; 356/32
(58) Field of Search ........................... 73/587, 588, 579, 73/584, 763, 778, 774, 801, 799; 356/32

(56) References Cited

U.S. PATENT DOCUMENTS

| 4,344,326 | 8/1982 | Kahn ........................................ 73/587 |
| 4,562,736 | * 1/1986 | Iwasaki et al. ......................... 73/587 |
| 5,164,669 | * 11/1992 | Namkung et al. .................... 324/209 |

FOREIGN PATENT DOCUMENTS

358221162A  * 12/1984 (JP) ...................................... 425/114
359224660A  * 12/1984 (JP) ....................................... 399/46

* cited by examiner

Primary Examiner—Hezron Williams
Assistant Examiner—Rose M. Miller (57) ABSTRACT

Disclosed is a method for testing the photoinduced domain switching of ferroelectric ceramics using AE. A ferroelectric ceramic specimen 4 was tested for the AE signal and photovoltaic current upon application of light. Light emanating from a xenon lamp 1 is focused into a specimen 4 through a waveguide 2 and a lens 3. Raw AE signals are detected through an AE sensor 5. The output signals from the AE sensor 5 are forwarded to a bandpass filter 7 which filtered the signals. Then, the AE signals are amplified by 40 dB by a pre-amplifier 8 and further by 30 dB by an AET 5500 system 10 which is connected to a computer 9 for analyzing the signals. The AE events which show a peak amplitude greater than or as great as a predetermined threshold voltage are counted with respect to an irradiation period of time, followed by calculating an occurrence rate of the AE event counts. From these data, the activity of the photoinduced domain switching can be qualitatively evaluated. The energy of the AE signals is calculated from the formula: AE Energy(dB)=Peak Amplitude(dB)+10 log Duration Time ($\mu$s), so as to recognize the distributions of the energy. By investigating the types of domain switching which exist in the energy distributions, to which types of domain switching the AE signals are attributed can be determined.

12 Claims, 7 Drawing Sheets

METHOD FOR TESTING PHOTOINDUCED DOMAIN SWITCHING OF FERROELECTRIC CERAMICS USING ACOUSTIC EMISSION

BACKGROUND OF THE INVENTION

1. Field of the Invention

The present invention relates to a method for testing the domain switching induced in ferroelectric ceramics upon light irradiation, with the aid of an acoustic emission technique. Since photoinduced domain switching causes a change in the remanent polarization and strain of ferroelectric ceramics, the test thereof is very important in controlling optical properties such as photovoltaic currents and photostrains.

2. Description of the Prior Art

Being defined as the phenomenon of transient elastic-wave generation due to a rapid release of strain energy caused by a certain event, such as a structural alteration, in a solid material, acoustic emission (hereinafter referred to as "AE") is useful to non-destructively analyze the dynamic action generated in the material, in real time. AE is known to be used for monitoring the domain switching generated in ferroelectric materials under the influence of external electric fields, as reported by W. Pan and H. Cao (Ferroelectrics, 129, 119 (1992)) and Y. Saito and S. Hori (Jpn. J. Appl. Phys., 33, 5555 (1994)).

Generally, photoinduced domain switching phenomena are observed by generating and switching 180° domains in ferroelectric single crystals, such as SbSI, $BaTiO_3$ and $PbTiO_3$, with the aid of an optical microscope. They are caused by the screening effect of photoinduced electrons on spontaneous polarization, as analyzed in reports (V. M. Fridikin, A. A. Grekov, N. A. Kosonogov and T. R. Volk, Ferroelectrics, 4, 169 (1972); A. Semenchev, V. Gavrilyatchenko and E. Fesenko, Ferroelectrcs, 157, 135 (1994)).

In ferroelectric polycrystal ceramics, on the other hand, there exist grain boundaries in which photoinduced non-equilibrial electrons can be entrapped, forming a space charge field over each grain, as reported by Land et al. (C. E. Land and P. S. Peercy, Ferroelectrics, 22, 677 (1978)). Expectedly, the space charge field is sufficient to cause the domain switching. However, since ferroelectric ceramics are composed of grains as small as several microns and the photoinduced domain switching is generated within a very shallow depth limited to the light-absorbed range, the domain switching is virtually difficult to observe with the aid of microscopes or by use of X-ray diffraction. In fact, research on the domain switching during the application of light is scarcely conducted. Related to the present invention is U.S. Pat. No. 4,344,326 with a disclosure of non-destructive testing of ferroelectric capacitors, but it is not concerned with domain switching.

SUMMARY OF THE INVENTION

With the aim of solving the problems encountered in prior arts and making it easy to observe the domain switching generated when irradiating ferroelectric ceramics, the present invention is directed to in-situ testing of the domain switching by use of an AE technique. In the present invention, the AE event counts generated when light is illuminated on a tetragonal structure of $(Pb_{1-z}La_x) TiO_3$ ferroelectric ceramic, are measured to test the activity of photoinduced domain switching against various experimental parameters. At the same time, the change in photovoltaic current of the material is monitored to confirm the reliability of the AE signals detected. Further, a tetragonal structure is found to retain two domains: 90° domain and 180° domain. On the basis of this finding, what the domain switching is, which is caused upon the application of light, can be determined through AE energy distributions using an AE technique.

Therefore, it is an object of the present invention to provide a method for testing the photoinduced domain switching of ferroelectric ceramics, which is simple and convenient.

In accordance with the present intention, the above object could be accomplished by a provision of a method for testing the photoinduced domain switching of ferroelectric ceramics by use of acoustic emission, comprising the steps of: focusing on a ferroelectric ceramic sample of a tetragonal structure a light beam which has an energy greater than or as great as a band gap, so as to induce electrons into conduction bands; detecting acoustic emission signals from the sample; filtering the raw acoustic emission signals; amplifying the filtered acoustic emission signals; and analyzing the amplified acoustic emission signals while measuring photovoltaic currents.

BRIEF DESCRIPTION OF THE DRAWINGS

The above and other objects, features and other advantages of the present invention will be more clearly understood from the following detailed description taken in conjunction with the accompanying drawings, in which:

FIG. 3a is a graph in which photovoltaic currents are plotted against irradiation periods of time for the ferroelectric ceramics of FIG. 2a;

FIG. 8a is a diagram showing the energy distribution of the AE signals of a ferroelectric ceramic sample of FIG. 7a.

DETAILED DESCRIPTION OF THE INVENTION

Below, details will be given of the constitution and operation of the present invention.

When light energy as great as or greater than a band gap is applied to ferroelectric ceramic, electrons are induced into the conduction bands. While moving in the direction of remanent polarization, some of the induced electrons are trapped in the boundaries among grains. On the other hand, the electrons still remaining in the conduction band give a bulk photovoltaic effect, generating a photovoltaic current (A. M. Glass, D. von der Linde, and T. J. Negran, Appl. Phys. Lett., 25, 233 (1974)). The electrons trapped in the grain boundaries form a space charge field over each grain, leading to the domain switching. This domain switching makes large the remanent polarization which the grains already have retained through the polarization and the magnified residual polarization gives rise to an increase in the photovoltaic current (C. E. Land and P. S. Peercy, ferroelectrics, 22, ←(1978)).

If the irradiation continues, the photoinduced, non-equilibrial electrons further move in the direction of the remanent polarization and are also trapped in grain boundaries to form larger space charge fields. Thus, the domain switching continues to occur while a nonsteady state photovoltaic current increases with the illumination period of time. A series of such physical events are repeated (S. R. Kim, Thesis, Korea Advanced Institute of Science and Technology (1998)) until the strain energy accumulated within the grains due to the domain switching is so large as to refrain from domain switching further.

During illumination, at any rate, the domain switching attributed to the space charge field allows the detection of AE signals, increasing the remanent polarization which is proportionally associated with the photovoltaic current.

A better understanding of the present invention may be obtained in light of the following examples. However, the examples are set forth to illustrate with ferroelectric ceramics of $(Pb_{1-x}La_x)TiO_3$ compositions, but are not to be construed to limit the present invention. Regardless of composition type, ferroelectric ceramics, if they are of domain structures, can be tested for the domain switching upon illumination by the present invention using AE.

EXAMPLE

Figure 1:
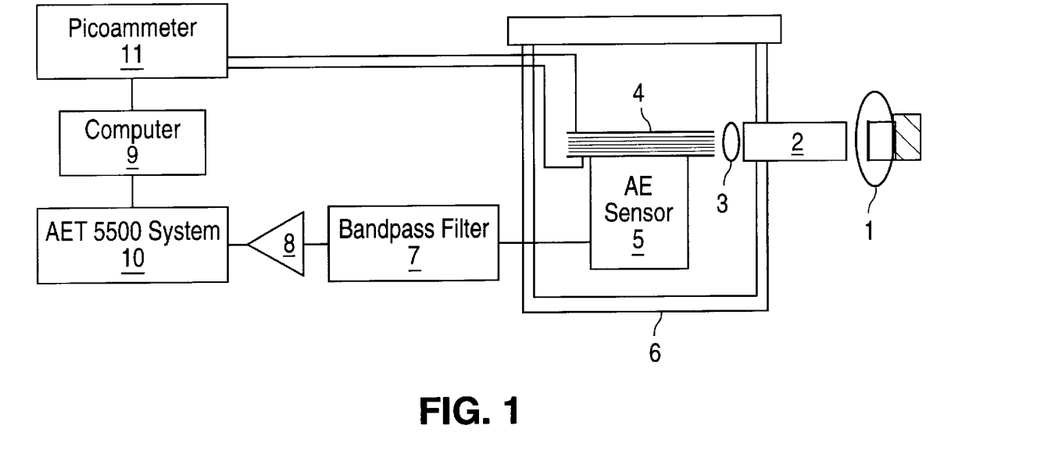
FIG. 1 is a diagram showing the testing apparatus capable of measuring the acoustic emission signals and photovoltaic currents, simultaneously, attributed to the domain switching of ferroelectric ceramics during the application of light.

Using AE processing equipment whose particular system used in the exemplary example is shown in FIG. 1, a ferroelectric ceramic specimen 4 was tested for the AE signal and photovoltaic current upon application of light. The light emanating from a 300 W xenon lamp 1 was focused into the specimen 4 through a waveguide 2 and a lens 3. The specimen 4 was 19 mm in diameter with a thickness of 4 mm, on the opposite surfaces of which gold was deposited by a sputtering method. Raw AE signals were detected through a 175 kHz resonant AE sensor 5. The output signals from the AE sensor 5 were forwarded to a bandpass filter 7 which filtered the signals in the frequency range of 125 to 1,000 kHz. Then, the AE signals were amplified by 40 dB by a pre-amplifier 8 and further by 30 dB by an AET 5500 system 10 which was connected to a computer 9 for analyzing the signals. Threshold voltage was set at a level of 0.1 V. As for photovoltaic current, it was measured by use of a Keithley 486 Picoammeter 11 during the detection of the AE signals.

Test Example I

Two species of $(Pb_{0.85}La_{0.15})TiO_3$ ferroelectric ceramics with a grain size of 4.2 μm and 7.3 μm, each, underwent a poling process at a poling field of 0.5 kV/mm, 1.0 kV/mm, 1.5 kV/mm and 2.0 kV/mm. Under a light intensity of 2.1 W/cm², the cumulative AE counts which took place with the irradiation period of time, were determined, and the results are given in FIGS. 2a and 2b.

Figure 2A:
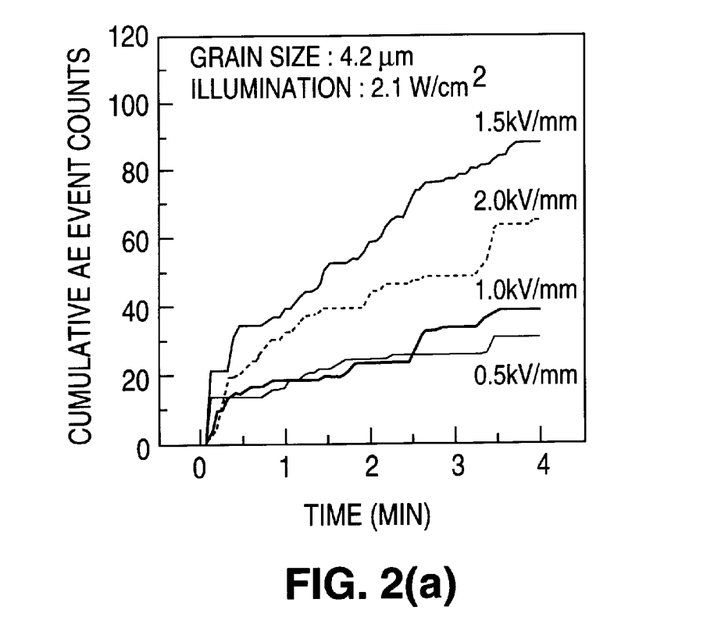
FIG. 2a is a graph in which cumulative AE event counts are plotted against irradiation periods of time for the ferroelectric ceramics with a grain size of 4.2 $\mu$m which have undergone a poling process at 0.5 kV/mm, 1.0 kV/mm, 1.5 kV/nm and 2.0 kV/mm.
Figure 2B:
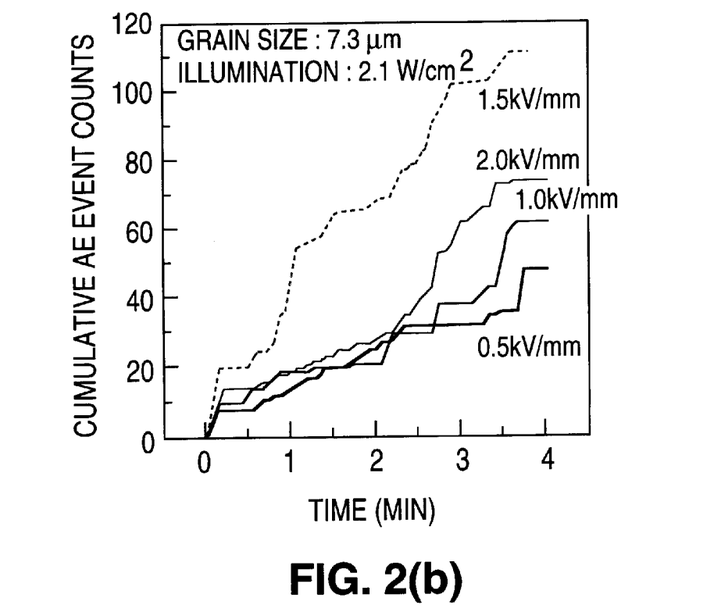
FIG. 2b is a graph in which cumulative AE event counts are plotted against irradiation periods of time for the ferroelectric ceramics with a grain size of 7.3 $\mu$m which have undergone a poling process at 0.5 kV/mm, 1.0 kV/mm, 1.5 kV/nm and 2.0 kV/mm.

As seen in the plots, the cumulative AE event counts increase with the irradiation period of time, irrespective of the grain size and the poling field, but their increasing behaviors for an irradiation period of 4 min are dependent on these factors. The observed AE signals all were attributed to the photoinduced domain switching in the ferroelectric ceramic 4 on the basis of the fact that, in the present invention, the AE signals generated due to the micro-cracks in the specimen and the interaction with external electric fields can be extruded.

Test Example II

Figure 3A:
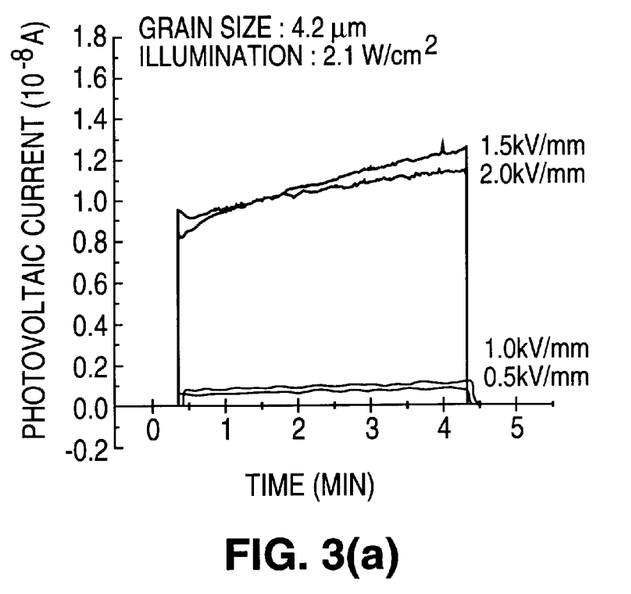
Figure 3B:
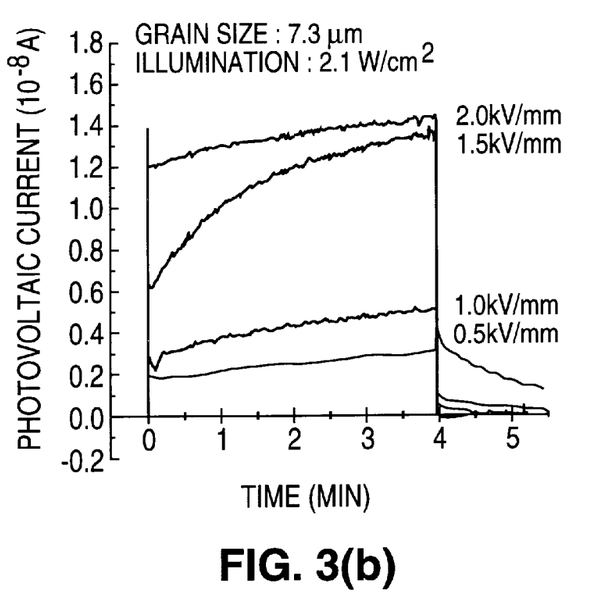
FIG. 3b is a graph in which photovoltaic currents are plotted against irradiation periods of time for the ferroelectric ceramics of FIG. 2b.

When AE signals were detected in Test Example I, the change in photovoltaic current was also plotted against the irradiation period of time. The results are given in FIGS. 3a and 3b. As shown in the plots, the photovoltaic current increases with the irradiation time period at an initial stage, regardless of the grain size and poling field, to a saturation level at 4 min after the irradiation. However, the absolute value and increase rate of the photovoltaic current depend on the grain size and poling field.

Test Example III

Figure 4A:
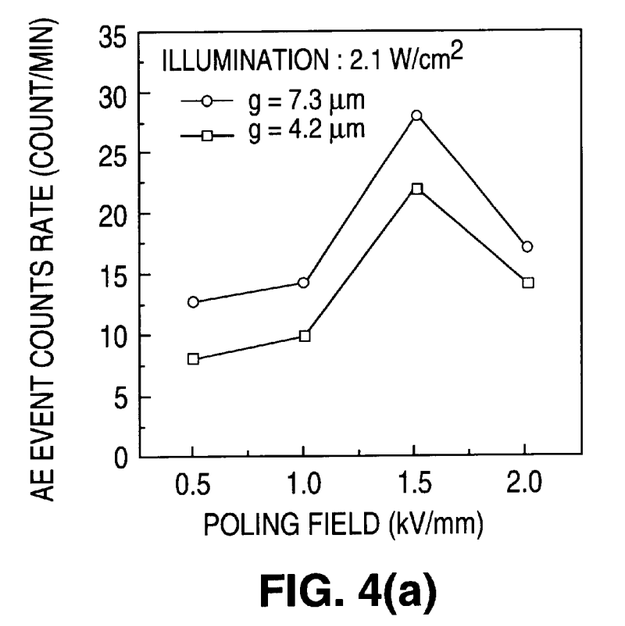
FIG. 4a is a graph in which average values of the AE event counts measured in FIG. 2 are plotted with respect to the polarization fields.
Figure 4B:
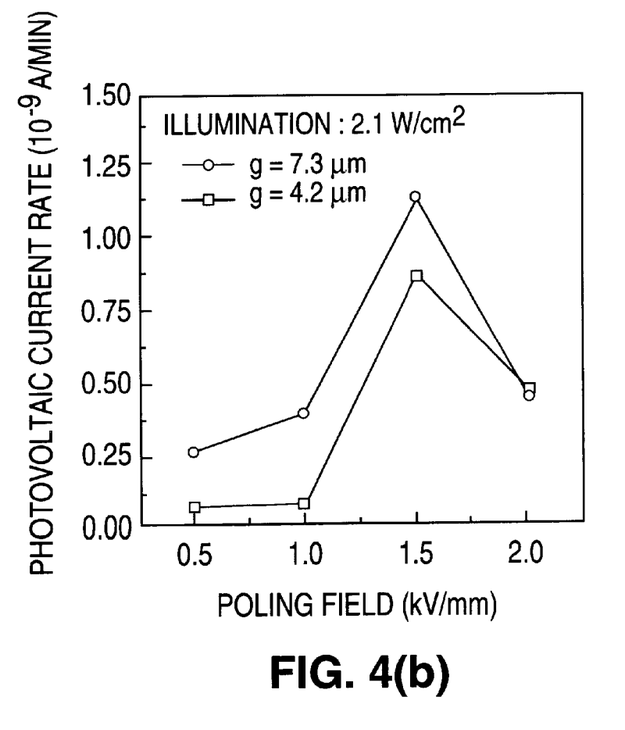
FIG. 4b is a graph in which average values of the photovoltaic currents measured in FIG. 3 are plotted with respect to the polarization fields.

For the specimens 4.2 μm and 7.3 μm in size, the occurrence rate of AE event counts and the increase rate of photovoltaic currents were plotted against poling fields. The results are given in FIGS. 4a and 4b, respectively. As shown in FIGS. 4a and 4b, the increase rate of photovoltaic currents followed the behavior through which the occurrence rate of AE event counts went, indicating that the occurrence of AE event count and the increase in photovoltaic current were based on he photoinduced domain switching. Thus, the occurrence rate and the increase rate reflect the activity of the photoinduced domain switching with a maximum level at a polarization field of 1.5 kV/mm. Further, greater activity of photoinduced domain switching was obtained from the 7.3 μm specimen than from the 4.2 μm specimen over the polarization field range examined, indicating that ferroelectric ceramics consisting of larger grains have higher activity of photoinduced domain switching.

Test Example IV

Figure 5:
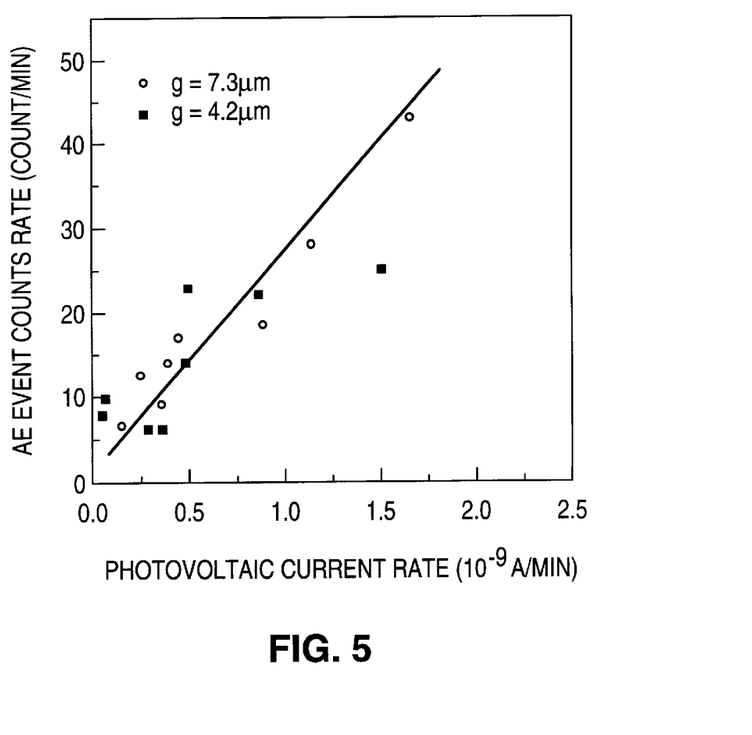
FIG. 5 is a graph showing the correlation between the occurrence rate of the AE event counts of FIG. 4a and the increase rate of the photovoltaic currents of FIG. 4b, incorporating the data measured at a light intensity of 2.5 $W/Cm^2$.

Based on the data of FIG. 4, obtained under a light intensity of 2.1 W cm², and the data obtained under a light intensity of 2.1 W/cm², the correlation between the occurrence of AE event count and the increase rate of the photovoltaic current is summarized in FIG. 5. On the whole, as seen in FIG. 5, the occurrence rate of AE event count is proportional to the increase rate of photovoltaic current. From this proportional correlation, it should be noted that, by monitoring and counting AE signals from ferroelectric ceramics during the application of light, the optical properties of the materials may be determined by comparing the monitored counts to the calibration curve between the occurrence of AE event counts and the photovoltaic current or photostrain increase.

Test Example V

On the basis of the report revealing that no 90° domain structures exist in the compositions at a tetragonal ratio of about 1 (G. King and E. K. Goo, J. Amer. Cera. Sci., 73, 1534, (1990)), a measurement was made of the AE signal and photovoltaic current for $(Pb_{0.85}La_{0.15})TiO_3$ (PLT15) and $(Pb_{0.76}La_{0.24})TiO_3$ (PLT24), which are 1.021 and 1.007 in the tetragonal ratio of $(Pb_{1-x}La_x)TiO_3$, respectively, in order to examine which type the photoinduced domain switching occurring in $(Pb_{1-x}La_x)TiO_3$ ferroelectric ceramics belongs to.

Figure 6A:
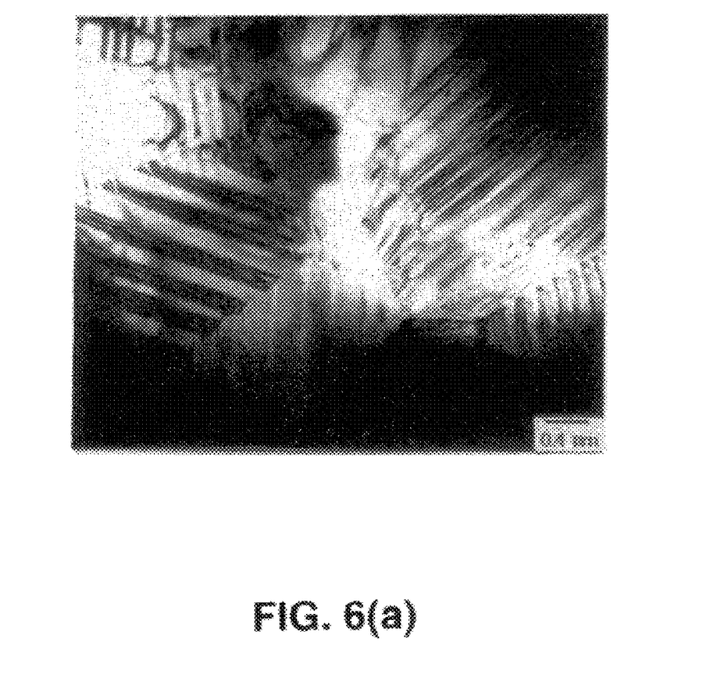
FIG. 6a is a transmission electron microphotograph showing the domain structure of a ferroelectric ceramic specimen with a tetragonal ratio of 1.021.
Figure 6B:
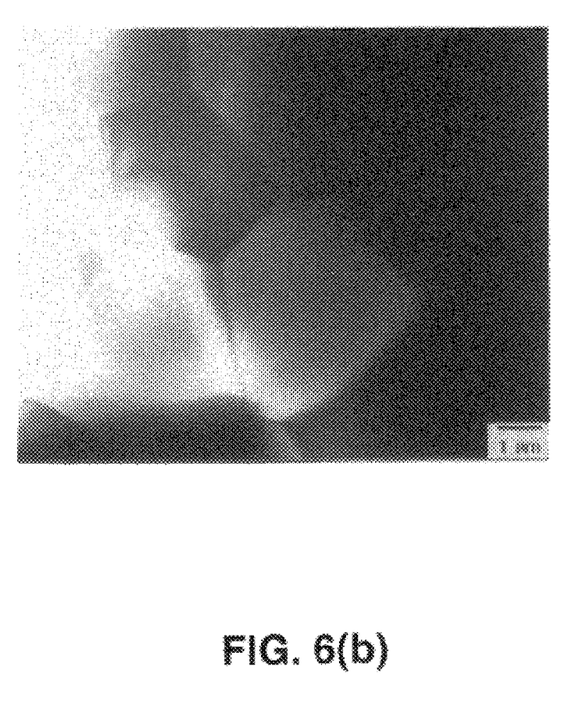
FIG. 6b is a transmission electron microphotograph showing the domain structure of a ferroelectric ceramic specimen with a tetragonal ratio of 1.007.

With reference to FIG. 6, there are transmission electron microphotographs showing the domain structures of the ferroelectric ceramics with a larger tetragonal ratio (PLT15) and a smaller tetragonal ratio (PLT24). A well known twin structure of 90° domains was favorably developed in the PLT15 as seen in FIG. 6a. On the other hand, the twin structure, which is evident of the existence of 90° domains, was not found in the PLT24 small in tetragonal ratio. Only the difference in brightness between grains could be observed owing to the influence of 180° domains. Therefore, 90° and 180° domains both are well developed in the PLT15 specimen with a large tetragonal ratio while 180° domains quite predominate in the PLT24 specimen having a tetragonal ratio of nearly 1.

Test Example VI

Figure 7A:
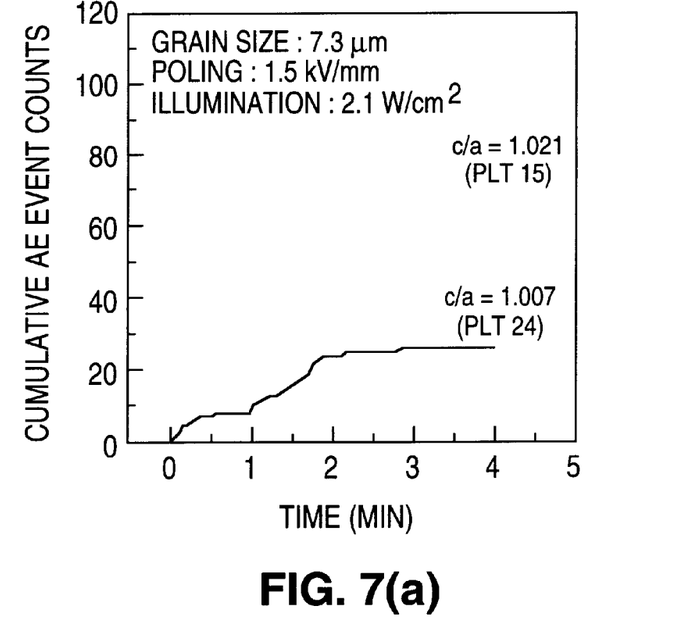
FIG. 7a is a graph in which the cumulative AE event counts generated in ferroelectric samples with a grain size of 7.3 μm are plotted against the irradiation periods of time for tetragonal ratios.
Figure 7B:
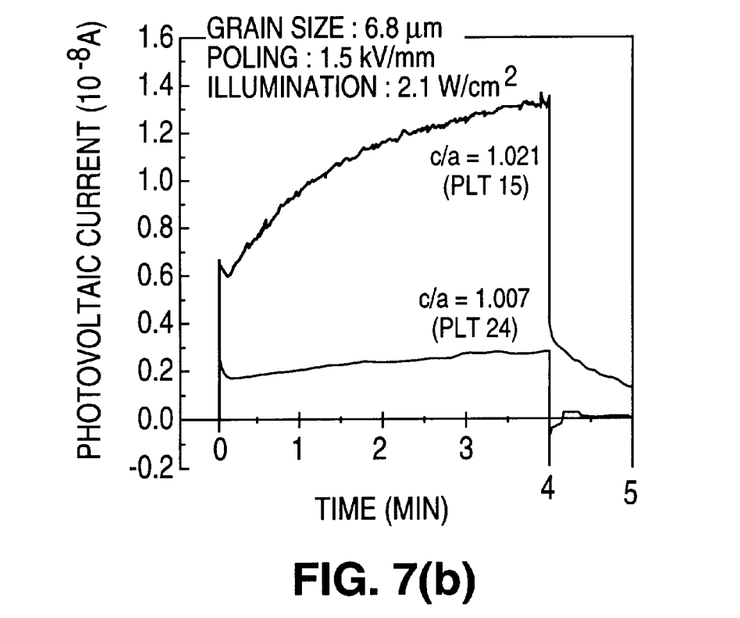
FIG. 7b is a graph in which the photovoltaic currents generated in ferroelectric samples with a grain size of 6.8 μm are plotted against the irradiation periods of time for tetragonal ratios.

After undergoing a poling process at 1.5 kV/mm, PLT15 and PLT24 specimens were irradiated at a light intensity of 2.1 W/cm². For time being, an examination was made of the cumulative AE event count and photovoltaic current of each of the specimens, and the results are given in FIGS. 7a and 7b. Regardless of the grain sizes (7.3 μm and 6.8 μm), as shown in the figures, the material (PLT15) with a larger tetragonal ratio shows greater changes in cumulative AE event count and photovoltaic current with respect to the irradiation period of time, indicating that more active domain switching takes place in the materials with larger tetragonal ratios.

Test Example VII

Figure 8A:
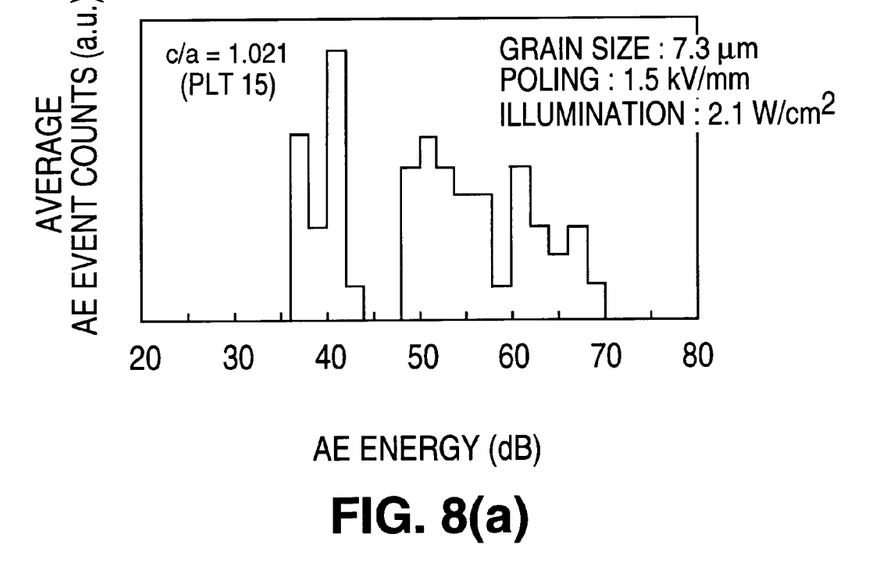
Figure 8B:
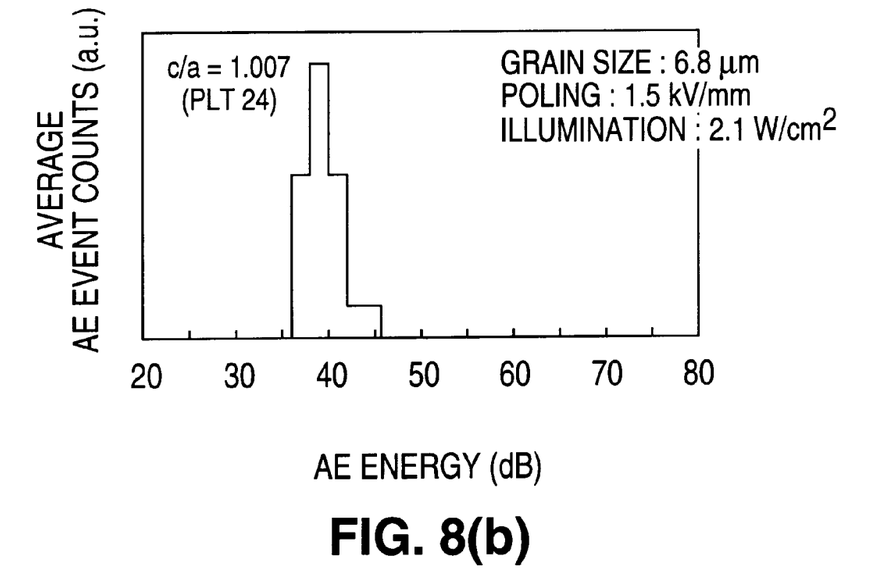
FIG. 8b is a diagram showing the energy distribution of the AE signals of a ferroelectric ceramic sample of FIG. 7b.

For the same two specimens (7.3 μm PLT15 and 6.8 μm PLT24) as those used in Test Example VI, energy distributions of AE signals were measured and compared as shown in FIGS. 8a and 8b. As a function of peak amplitude and duration time, the AE energy was calculated according to the following formula:

AE Energy(dB)=Peak Amplitude(dB)+10 log Duration Time(μs)

In the material with a large tetragonal ratio (PLT15), as seen in FIG. 8a, there are two groups of energy distributions: one is a narrow distribution in the vicinity of 40 dB; the other distribution extends from about 50 to 70 dB. On the other hand, the material with a small tetragonal ratio (PLT24) has only the low energy distribution around 40 dB. As proved in FIGS. 6a and 6b, the material with a large tetragonal ratio is almost full of 180° domains while the material with a small tetragonal ratio retains 90° domains and 180° domains in combination. Thus, the low energy distribution and the high energy distribution consist of the AE signals which are based on 180° domain switching and 90° domain switching, respectively. Consequently, according to the present invention, what the domain switching is, which takes place in ferroelectric ceramics due to the space charge field during the application of light, can be recognized on the basis of the AE energy distributions.

As described hereinbefore, the present invention provides a method by which the domain switching occurring in ferroelectric ceramics during irradiation can be effectively tested. According to the testing method, any material, if having a domain structure, can be subjected to AE event counting during irradiation, regardless of experimental parameters, such as poling field, grain diameter and light intensity, to test the occurrence rate of domain switching and thus the optical properties of the material. Further, the analysis of AE energy distribution provides information about whether the AE signals are due to 90° domain switching or 180° domain switching.

The present invention has been described in an illustrative manner, and it is to be understood the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for testing the photoinduced domain switching of ferroelectric ceramics by use of acoustic emission, comprising the steps of:

focusing a light beam on a ferroelectric ceramic sample of a tetragonal structure, the light beam having an energy greater than or as great as a band gap to induce electrons into conduction bands;

detecting acoustic emission signals from the sample;

filtering the raw acoustic emission signals;

amplifying the filtered acoustic emission signals;

measuring photovoltaic currents from the sample; and analyzing the amplified acoustic emission signals and the measured photovoltaic currents to provide an indication of the photoinduced domain switching.

2. A method as set forth in claim 1, wherein the light beam is generated from a xenon lamp and goes through a waveguide and a lens to the sample.

3. A method as set forth in claim 1, wherein the detecting step is carried out with the aid of an acoustic emission sensor.

4. A method as set forth in claim 1, wherein the filtering step is carried out with the aid of a bandpass filter.

5. A method as set forth in claim 1, wherein the amplifying step is carried out twice with the aid of a pre-amplifier for the first and an AET 5500 system for the second.

6. A method as set forth in claim 1, wherein the analyzing step is carried out with the aid of a computer while the photovoltaic currents are measured by use of a Keithley 486 Picoammeter.

7. A method as set forth in claim 1, wherein the analyzing step comprises counting the acoustic emission events which show peak amplitude greater than or as great as a predetermined threshold voltage with respect to an irradiation period of time, calculating an occurrence rate of the acoustic emission event counts, and qualitatively evaluating the activity of the photoinduced domain switching from the occurrence data.

8. A method as set forth in claim 1 or 7, wherein the analyzing step further comprises counting AE signals from the ferroelectric ceramics during the application of light and comparing the monitored counts to a calibration curve to predict the change rate of the photovoltaic current, said calibration curve being previously prepared between the occurrence of AE event counts and the photovoltaic currents measured.

9. A method as set forth in claim 1, wherein the analyzing step further comprises calculating the energy of the acoustic emission signals to recognize the distributions of the energy, investigating the types of domain switching which exist in the energy distributions, and determining to which types of domain switching the acoustic emission signals are attributed.

10. A method as set forth in claim 9, wherein the energy is calculated as follows:

$$AE\ Energy(dB) = Peak\ Amplitude(dB) + 10\ \log\ Duration\ Time(\mu s).$$

11. A method as set forth in claim 9, wherein the distributions of the energy are divided into a narrow, low energy region around 40 dB and a wide, high energy region extending from about 50 to 70 dB.

12. A method as set forth in claim 11, wherein the acoustic emission signals are attributed to 180° domain switching in the low energy region and to 90° domain switching in the high energy region.

* * * * *